US006676903B2

(12) United States Patent
Potyrailo et al.

(10) Patent No.: US 6,676,903 B2
(45) Date of Patent: Jan. 13, 2004

(54) APPARATUS AND METHOD FOR SPATIALLY DETECTING OR QUANTIFYING CHEMICAL SPECIES

(75) Inventors: Radislav Alexandrovich Potyrailo, Schenectady, NY (US); Timothy Mark Sivavec, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 219 days.

(21) Appl. No.: 09/917,349

(22) Filed: Jul. 30, 2001

(65) Prior Publication Data

US 2003/0040118 A1 Feb. 27, 2003

(51) Int. Cl.[7] .............................................. G01N 21/47
(52) U.S. Cl. ................................ 422/82.05; 422/82.09; 436/52; 436/53; 436/164; 436/169
(58) Field of Search ........................... 422/82.05–82.11, 422/68; 436/162, 164, 110, 124, 140, 52

(56) References Cited

U.S. PATENT DOCUMENTS

| | | | |
|---|---|---|---|
| 4,666,672 A | * 5/1987 | Miller et al. ............. | 422/82.07 |
| 4,771,006 A | 9/1988 | Miller et al. | |
| 4,929,562 A | 5/1990 | Anderson, deceased et al. | |
| 4,969,998 A | 11/1990 | Henn | |
| 5,059,790 A | * 10/1991 | Klainer et al. ......... | 250/227.21 |
| 5,145,583 A | 9/1992 | Angleraud et al. | |
| 5,268,972 A | * 12/1993 | Tabacco et al. ............. | 385/12 |
| 5,290,704 A | 3/1994 | Chang | |
| 5,434,084 A | * 7/1995 | Burgess, Jr. ............. | 436/52 |
| 5,547,877 A | 8/1996 | Friedman et al. | |

FOREIGN PATENT DOCUMENTS

EP 0928966 A1 * 7/1999

OTHER PUBLICATIONS

Donner et al.: "Transition from laboratory to on–site environmental monitoring of 2,4,6–trinitroluene using a portable fiber optic biosensor", ACS Symposium Series (1997), 657(Immunochem. Technology for Environmental Applications), 198–209, Abstract.*

Bakaltcheva et al. "Multi–analyte explosive detection using a fiber optic biosensor", Analytica Chimica Acta (1999), 399(1–2), 13 20, Abstract.*

Sano et al. "Fluorometric determination of aromatic aldehydes with 1,4–dimethyl–3–carbamoylpyridinium chloride", Analytical Sciences (1987), 3(4), 359–62, Abstract.*

Gladilovich et al. "Fluorometric determination of aromatic aldehydes with 1,2–diaminobenzene", Zhurnal Analiticheskoi Khimii (1989), 44(7), 1329–32, Abstract.*

(List continued on next page.)

Primary Examiner—Jill Warden
Assistant Examiner—Yelena Gakh
(74) Attorney, Agent, or Firm—Toan P. Vo; Patrick K. Patnode

(57) ABSTRACT

An apparatus provides for the detection, the determination of the location or the spatial distribution, and/or the quantification of an amount of a chemical species by allowing the chemical species to come into contact with a fluid medium contained in a permeable capillary, transferring the content of the capillary after the contact to a detector, and detecting the chemical species as the content of the capillary is transferred to a detector. The fluid medium can contain a selected reagent that selectively interacts with the chemical species to produce an optically detectable interaction product. The location and amount of the chemical species are determined from a characteristic of the chemical species or its interaction product measured on the content of the capillary and the time at which the characteristic is detected. The apparatus may be used in a method for detecting, determining the location or the spatial distribution of, and quantifying a wide range of chemical compounds, such as for monitoring chemicals in environment and industrial facilities and determining products in a combinatorial experiment.

24 Claims, 3 Drawing Sheets

OTHER PUBLICATIONS

D. J. Glover and E. G. Kayser, "Quantitative Spectrophotometric Analysis of Polynitroaromatic Compounds by Reaction with Ethylenediamine," Analytical Chemical, vol. 40, No. 13, 2055–2058.

D. M. Colman, "Paper Chromatography of Substituted Trinitrobenzenes," Analytical Chemistry, vol. 35, No. 6, pp. 652–654, (1963).

C. A. Brown, Darcy H. Tarrant, Marta S. Olteanu, Joseph W. Mullens, and Eric L. Chronister, "Intrinsic Sol–Gel Clad Fiber–Optic Sensors with Time–Resolved Detection," Analytical Chemical, vol. 68, No. 4, pp. 2289–2295, (1996).

G. A. Lugg, "Fujiwara Reaction and Determination of Carbon Tetrachloride, Chloroform, Tetrachloroethane, and Trichloroethylene in Air," Analytical Chemistry, vol. 38, No. 11, pp. 1532–1536, (1966).

J. M. Henshaw, Lloyd W. Burgess, Karl S. Booksh, and Bruce R. Kowalski, "Multicomponent Determination of Chlorinated Hydrocarbons Using a Reaction–Based Chemical Sensor. 1. Multivariate Calibration of Fuiwara Reaction Products," Analytical Chemistry, vol. 66, No. 20, pp.

E. Sawicki, "Photometric Organic Analysis Part 1," pp. 483, 568–573, 577–581, 614, John Wiley & Sons, Inc., NY (1970).

R. A. Potyrailo and G.M. Hieftje, "Spatially Resolved Analyte Mapping with time–of–flight Optical Sensors," Trends in Analytical Chemistry, vol. 17, No. 10, pp. 593–604, (1998).

M. Richardson, "Spectrophotometric Micro–Estimation of Some Simple Plant Amines," Nature, vol. 197, pp. 290–291, (Jan. 1963).

G. P. Arsenault and W. Yaphe, "Effect of Acetaldehyde on the Resorcinol Test for Fructose," Nature, vol. 197, No. 4863, pp. 181–182, (Jan. 1963).

* cited by examiner

APPARATUS AND METHOD FOR SPATIALLY DETECTING OR QUANTIFYING CHEMICAL SPECIES

CROSS REFERENCE TO RELATED APPLICATIONS

The present patent application is related to patent application Ser. No. 09/441,851; titled "Poly(1,4-ethylene-2-piperazone) Composition, Method for Production of a Poly (1,4-ethylene-2-piperazone) Composition, TCE Detecting Method and Sensor," filed on Nov. 17, 1999; now U.S. Pat. No. 6,461,872.

BACKGROUND OF THE INVENTION

The present invention relates to an apparatus and a method for detecting, ascertaining the location of, or quantifying chemical species using selective chemical interaction and selective chemical detection. More particularly, the present invention relates to an apparatus and a method for in-situ detecting or quantifying chemical species using selective chemical interaction and detection of products of such chemical interaction and selectively spatially resolved chemical detection of analytes.

As industrial and commercial activities continue to accelerate, many manmade chemical species have found their way into the environment, heightening concern about human health and safety. Halogenated hydrocarbons that have been used as industrial solvents, medium for extraction of natural products, degreasing agents, dry cleaning fluids, refrigerants, fuel additives, fumigants, and intermediates for the synthesis of a multitude of other organic compounds have appeared in ground water at numerous locations. Other chemical compounds, such as explosives and rocket propellants, have contaminated soil at and migrated beyond manufacturing sites. Concern about the health effects of chemical compounds such as these in the environment has led to the quest for better methods for detecting and monitoring their presence. Many chemical species interact with other chemical compounds to yield products that have identifiable characteristics, providing reliable identification thereof. Detection methods for these products relying on these characteristics include optical (refractive index, scattering, etc.), spectroscopic (UV-visible ("UV-VIS") electronic absorbance, Raman, luminescence, infrared, near infrared), electrochemical, gravimetric, mass spectrometric, and other types of detection known in the art. Many colorless or optically transparent chemical species react with selected reagents to yield colored or fluorescent products, which can provide the basis for the detection of such chemical species.

One such method of detection is based on the reaction of halogenated hydrocarbons with pyridine or pyridine derivatives in an alkaline medium to yield red colored products in what has been commonly known as the Fujiwara reaction.

Many other compounds react with selected reagents to yield products that absorb electromagnetic ("EM") radiation in the wavelength range from ultraviolet ("UV") to infrared ("IR"). For example, some polynitroaromatic compounds react with ethylenediamine to yield products that absorb at wavelength of about 455 nm or about 530–560 nm.

The optical effects of selective chemical interaction have been incorporated in optical fibers for the determination of the location or the spatial distribution of selected chemical compounds by measuring the backpropagated EM radiation. Such method is known as "optical time-domain reflectometry" or "OTDR." For example, a fiber-optic waveguide having an aluminosilica xerogel clad was used to detect the spatial distribution of quinizarin (1,4-dihydroxyanthraquinone) (C. A. Browne et al., "Intrinsic Sol-Gel Clad Fiber-Optic Sensors With Time-Resolved Detection," Anal. Chem., Vol. 68, No. 14, 2289 (1996)). Quinizarin adjacent to the optical fiber sensor complexes with aluminum in the clad to yield a product that strongly absorbs EM radiation at wavelength of about 560 nm. Therefore, a measurement of the light intensity at wavelength of 560 nm and the arrival time at the detector of the return light of a pulse of light launched into the fiber-optic waveguide indicates the concentration and the location of quinizarin.

However, the basic OTDR method has several disadvantages that limit its appeal in chemical detection. The most important disadvantage is the low intensity of detected backpropagated radiation which can be $10^2$–$10^5$ times weaker than the forward traveling pulse. As a result, recording a useful signal of backpropagated radiation requires sophisticated detection schemes, high-power lasers, and time-consuming signal-averaging techniques. Frequently, signal integration times are in the range of several tens of minutes and involve averaging $10^5$–$10^7$ waveforms. Several methods have been devised and demonstrated to raise the levels of these signals. These methods include those based on pseudonoise, polarimetry, and nonlinear optical effects. Unfortunately, these techniques are limited to the use of single-mode optical fibers which are very difficult to implement for chemical detection.

Therefore, there is a continued need for simple apparatuses and convenient methods for detecting, determining the location or the spatial distribution of, and quantifying chemical species. It is also desirable to have such simple apparatuses and methods for readily implementing in the field.

SUMMARY OF THE INVENTION

The present invention provides an apparatus and a method for detecting the presence, determining the location or the spatial distribution, and quantifying an amount of at least one chemical species by allowing the chemical species to come into contact with a fluid medium spatially distributed in a defined container having a permeable wall with respect to the chemical species. The location or spatial distribution of the chemical species is thus determinable from the location of the sample of the fluid medium at the location within the container at which the contact occurs. In one preferred embodiment, the container is a capillary. The fluid medium can comprise at least one reagent with which the chemical species can undergo a selective chemical interaction after permeating the wall of the container. The apparatus and method of the present invention are easily implementable in the field. The term "chemical interaction," as used herein, refers to a coupling via a formation of permanent or temporary bonds between the chemical species and a selected reagent to yield a product species. The term "chemical interaction" includes, but is not limited to, chemical reaction, formation of chemical complexes, hydrogen bonding, and hydration.

An apparatus of the present invention comprises (1) a capillary the wall of which is permeable to at least one chemical species to be detected; (2) a means for delivering at least one fluid medium into the space inside the capillary; and (3) a means for transferring a content of the capillary to a detector for detecting the at least one chemical species. The detector provided in an apparatus of the present invention is at least one that employs a sensor or a method of detection selected from the group consisting of optical (refractive index or light scattering), spectroscopic (UV-VIS electronic absorbance, Raman, luminescence, infrared, or near infrared), electrochemical, gravimetric, mass spectrometric, and other sensors or methods known in the art.

According to one embodiment of the present invention, an apparatus of the present invention comprises (1) a capillary the wall of which is permeable to at least one chemical species to be detected; (2) a means for delivering at least one fluid medium into the space inside the capillary, the fluid medium comprising at least one reagent that is capable of undergoing a selective chemical interaction with the at least one chemical species to yield at least one optically detectable product; and (3) a means for transferring a content of the capillary to a detector for detecting the at least one optically detectable product, thereby detecting the at least one chemical species.

According to one aspect of the present invention, the detector is capable of quantitatively relating an optical signal that results from the presence of the interaction product to the amount of the chemical species outside the capillary. In another aspect of the present invention, the optical signal is an absorbance or an emission of electromagnetic radiation having a wavelength in the range of UV to IR (or from about 100 nm to about 1 mm).

A method of the present invention for detecting the presence, determining the location or the spatial distribution, and quantifying an amount of at least one chemical species comprises (1) providing a capillary in an area having the chemical species to be detected, the wall of the capillary being permeable to the chemical species; (2) delivering at least one fluid medium into the space inside the capillary; (3) allowing the chemical species to permeate through the wall of the capillary; (4) transferring a content of the capillary through a sensing element of a detector that is capable of detecting at least one characteristic of the chemical species; (5) measuring a magnitude of the characteristic and a time at which the characteristic is detected; and (6) relating the magnitude of the characteristic to an amount of the chemical species outside the capillary and the time at which the characteristic is detected to the location of the chemical species.

According to one aspect of the present invention, a method of the present invention for detecting the presence, determining the location or the spatial distribution, and quantifying an amount of at least one chemical species comprises (1) providing a capillary in an area having the chemical species to be detected, the wall of the capillary being permeable to the chemical species; (2) delivering at least one reagent into the space inside the capillary, the at least one reagent being capable of reacting or selectively interacting with the chemical species to be detected to yield at least one optically detectable product; (3) allowing the chemical species to permeate through the wall of the capillary and react or interact with the at least one reagent to yield the at least one optically detectable product; (4) transferring the content of the capillary through a sensing element of a detector that is capable of detecting at least one optical signal resulting from the presence of the at least one optically detectable product; (5) measuring a magnitude of the at least one optical signal and a time at which the at least one optical signal is detected; and (6) relating the magnitude of the optical signal to an amount of the chemical species outside the capillary and the time at which the optical signal is detected to the location of the chemical species.

According to one aspect of the present invention, a plurality of optical signals is detected. The times of detection of the plurality of the optical signals provide the spatial distribution of the chemical species along the capillary.

Other features and advantages of the present invention will be apparent from a perusal of the following detailed description of the invention and the accompanying drawings in which the same numerals refer to like elements.

DETAILED DESCRIPTION OF THE INVENTION

An apparatus and the method of the present invention are advantageously employed in detecting the presence of a wide range of chemical species, determining their locations or spatial distribution in a selected space, or quantifying their amounts at these locations. Unlike OTDR-based detection methods, the present invention does not rely on the transmission of light through a fiber-optic waveguide, or depend on a preservation of a high level of backpropagated light.

In general, an apparatus of the present invention comprises a defined container that contains a fluid medium and is located in a location where a chemical species is suspected to be present, means to deliver the fluid medium into the container, and means to transfer a content of the container to a sensing element of a detector that is capable of detecting a characteristic of the chemical species. In a preferred embodiment, the container is a capillary, the wall of which is permeable to the chemical species. When the content of the capillary is transferred continuously to the sensing element of the detector in a substantial plug flow, the time at which the characteristic of the chemical species is detected can be directly relatable to the location along the capillary at which the chemical species permeates through its wall. The detectable characteristic of the chemical species may be one of its own unique or identifiable characteristics or a characteristic of signal generated by a product of a selective interaction between the chemical species and the fluid medium or another chemical compound supplied with the fluid medium. The detectable characteristic of the chemical species or its interaction product may be detected by any number of known analytical method depending on the nature of the suspected chemical species or interaction product. Such an analytical method may employ a measurement of one of optical, spectroscopic, electrochemical, gravimetric, mass spectroscopic signal, and other signals recognizable in a specific application. A preferred method employs the detection of an optical signal such as absorbance at a characteristic wavelength generated by the presence of the chemical species or the interaction product.

Figure 1:
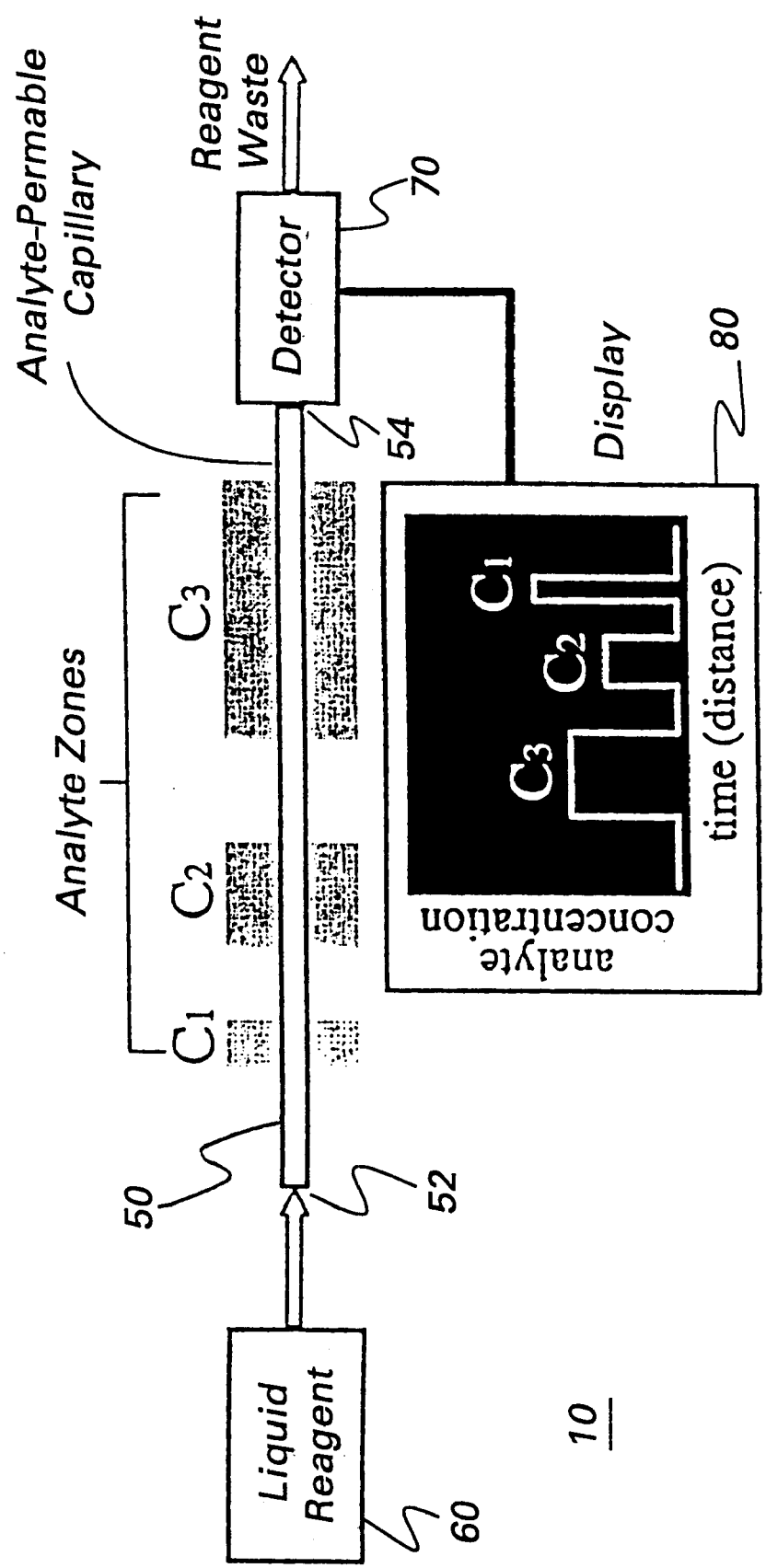
FIG. 1 is a schematic diagram of an apparatus of the present invention.

In an application of an apparatus 10 of the present invention, which is shown schematically in FIG. 1, one or more chemical species, such as denoted by $C_1$, $C_2$, and $C_3$, outside the capillary 50 diffuses or permeates through the wall of the capillary and reacts or interacts with a reagent 60 contained in the capillary 50 to yield a product that is capable of generating an optical signature identifiable with such product. Although FIG. 1 shows three chemical species or, alternatively, three locations of a chemical species, any number of chemical species or locations may be possible. The content of the capillary after a sufficient quantity of such product has been formed is conducted through the sensing element of a detector 70 in which the product yields a quantifiable optical signal that can be directly related to the amount of the chemical species and displayed on a display 80. The reagent 60 may be pure or diluted in a fluid medium and delivered to the capillary 50 by a pump or by creating a low pressure at one end of the capillary 50 and pulling the reagent 60 or the fluid medium through the other end of the capillary 50. The content of the capillary may be transferred or conducted through the sensing element of the detector by pumping an optically insensitive material into the capillary through one of its ends 52 and connecting the other end 54 of the capillary to the sensing element of the detector. Alternatively, the content of the capillary may be pulled through the sensing element of the detector by a suction pump or by creating a low pressure at the outlet end of the sensing element of the detector. When the content of the capillary is transferred continuously through the sensing element, the time at which the optical signature is detected is relatable to the position of the product in the capillary and, thus, the position of the chemical species along the capillary. In FIG. 1, chemical species $C_3$ is nearest to the detector sensing element and is detected first as it eludes out of the capillary 50. The reagent for a particular chemical species to be detected is preferably selected to yield a product that strongly absorbs EM radiation, such as UV, visible, or IR EM radiation. Alternatively, the product may emit detectable EM, especially in the visible spectrum. Preferably, the reagent is chosen such that the product of the reaction or interaction provides an optical signature substantially unique to the chemical species to be detected. An optical signature may be represented by a measurable optical signal. More than one optical signals, such as absorbances at two different wavelengths, may be measured to uniquely identify the chemical species.

In another embodiment of the present invention, at least a second detector is employed to analyze the content of the capillary to provide a second signature of the reaction product for further ascertaining the identification of the chemical species. Examples of such second detectors include, but are not limited to, those employing the principle of chromatography, such as gas chromatography ("GC"), or liquid chromatography ("LC"); mass spectrometry ("MS"); nuclear magnetic resonance ("NMR"); and atomic absorption ("AA").

The capillary may be made of any polymeric material that is permeable to the specific chemical species to be detected but resistant to damage by environmental conditions. Examples of suitable polymeric materials for producing a capillary of the present invention are polytetrafluoroethylene ("PTFE"), poly(vinyl chloride) ("PVC"), poly(vinyl alcohol) ("PVA"), polyurethane, polyolefins such as polyethylene or polypropylene, polycarbonate, polystyrene, polyamide, poly(vinylidene fluoride) ("PVDF"), polyarylsuphones, polyacrylonitrile, polyether, poly(ether thioether), poly(methyl methacrylate), poly vinylpyrrolidone, polysiloxane, copolymers thereof, TM and blends thereof. Two preferred polymeric materials are Nafion™ (a copolymer of perfluorosulfonic acid and polytetrafluoroethylene) and Teflon AF™ (a random copolymer of tetrafluoroethylene and perfluoro-2,2-dimethyl-1,3-dioxole). The capillary may be mesoporous (having pore size in the range from about 1 nm to about 100 nm) or microporous (having pore size in the range from about 100 nm to about 1000 nm). The pore size is selected so to obtain a reasonably rapid diffusion or permeation rate of the chemical species through the wall thickness of the capillary. The larger the molecular size of the chemical species, the larger the pore size should be. The pore size is preferably in the range from about 1 nm to about 200 nm; more preferably, from about 1 nm to about 50 nm. The polymeric material may be formed directly into capillary having an inner diameter in the range from about 2 micrometers to about 2 mm. Preferably, the capillary inner diameter is in the range from about 0.1 to about 1.5 mm. The wall thickness of the capillary is typically in the range from about 10 to about 200 micrometers, preferably from about 10 to about 150 micrometers. Alternatively, the porous polymeric material may be deposited on another porous support such as a porous glass capillary.

The capillary is filled with at least one reagent for selectively interacting with the chemical species. The reagent may be in a substantially pure state or may be diluted with a fluid medium that does not interact with the chemical species to be detected and does not interact with the capillary material. The capillary is filled by a means for delivering the substantially pure reagent or the mixture of the reagent and the fluid medium such as a pump. The capillary may also be filled by first evacuating the space inside the capillary using a vacuum pump and then allowing the reagent or the mixture of the reagent and the solvent to imbibe into the capillary internal space. Alternatively, the capillary also may be filled by gravity flow.

According to one aspect of the present invention, an apparatus of the present invention is used to detect, or to determine the spatial distribution of a chemical species in soil, and to quantify the amount of the chemical species at various depths in the soil. A small well is drilled into the ground to a desired depth where the chemical species is suspected to be present. A capillary having a corresponding length filled with a selective reagent is dropped into the well. Sufficient time is allowed for the reagent to react or interact with the chemical species to yield the optically detectable product. The content of the capillary is then pumped through the sensing element of the detector to detect the optical signal produced by the product. The times at which the optical signals occur are directly related to the distribution of the chemical species in the soil. The magnitude of each of the optical signals is related to the amount of the chemical species at the particular depth. More than one capillary made of different permeable materials, each containing a different reagent may be dropped into the same well for the detection of different chemical species that are likely to be in the well. In such a case, it may be desirable to flow the content of each capillary into a separate detector that is set to detect a different reaction product.

Other uses of the apparatus of the present invention are also envisioned. For example, the distribution of a chemical species in an area may be determined by laying the filled capillary on the area and determining the magnitude and the time of the optical signal as the content of the capillary is emptied through one of its ends after the reaction.

According to another aspect, an apparatus of the present invention is used to detect and to quantify the reaction product or products contained in each cell of an array of combinatorial chemical synthesis. In this case, each cell of the array is in contact with a discrete section of the filled capillary. The intensity of a signal generated by the presence of a particular chemical compound and the time when it is detected are related to the quantity of the chemical compound or another related to it and the particular cell of the array in which it is present or formed.

The following examples show compounds that may be detected and quantified by an apparatus and a method of the present invention.

Determination Of Trichloroethylene ("TCE")

The Applicants have discovered that TCE reacts with polyethylenimine to yield polyglycinamide in the presence of a strong base, such as sodium hydroxide according to Equation 1. Polyglycinamide can be quantitatively determined by an absorbance of 1R EM radiation at 6.03 micrometers (wave number of 1658 $cm^{-1}$).

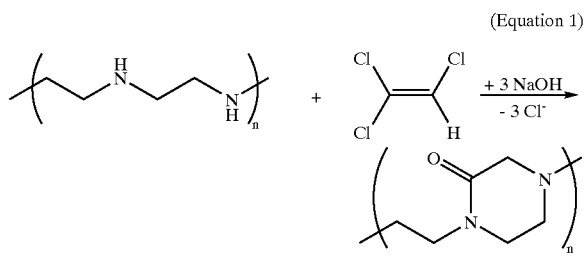

(Equation 1)

Similarly, N,N-dialkylethylenediamine also reacts with TCE to yield N,N-dialkylglycinamide in the presence of a strong base, such as sodium hydroxide according to Equation 2.

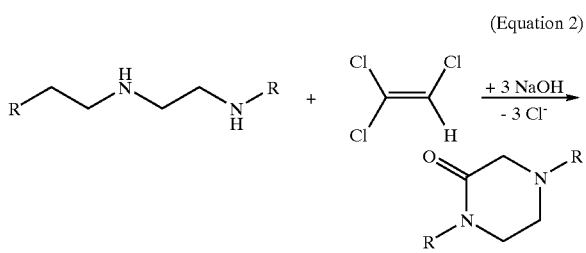

(Equation 2)

Figure 2:
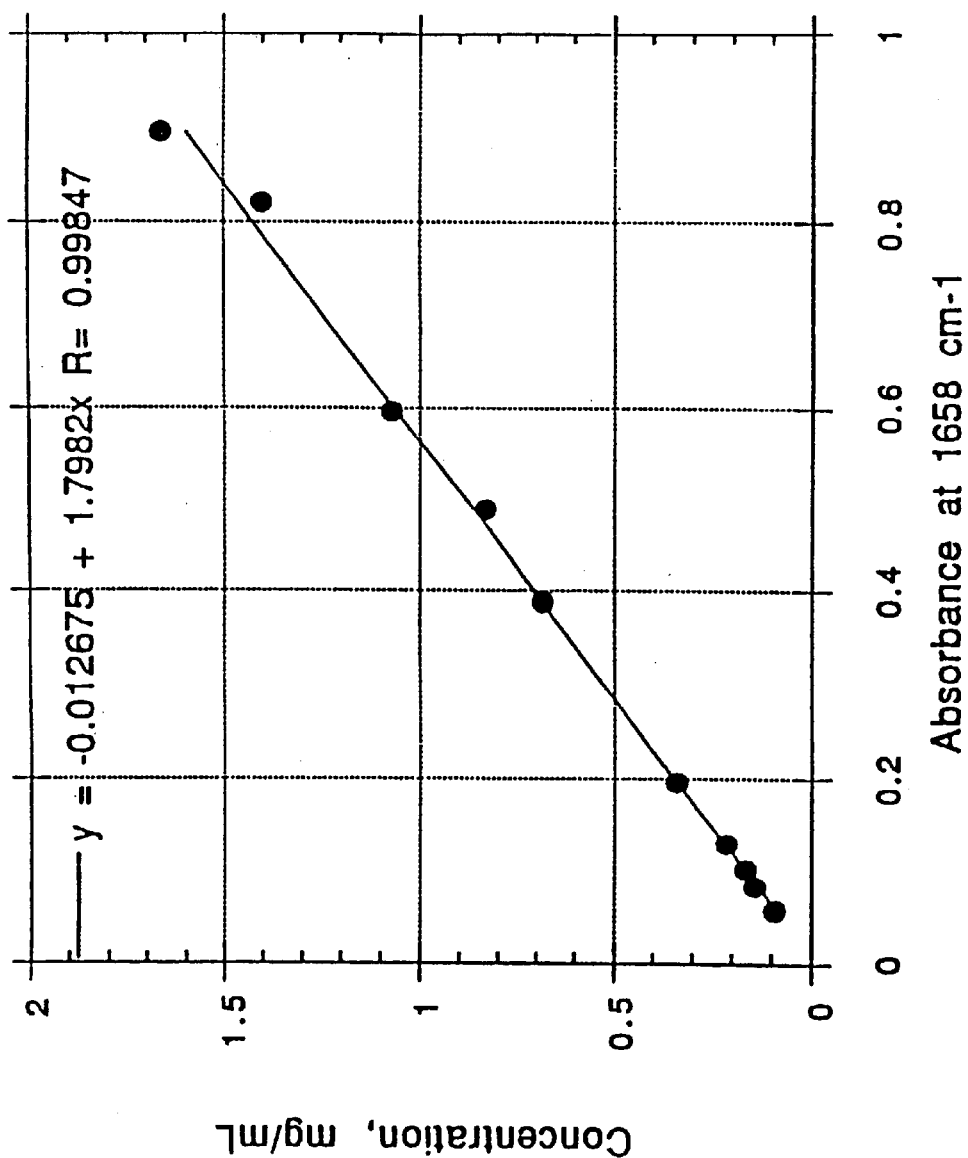
FIG. 2 is a calibration line showing the relationship between the IR absorbance of polyglycinamide at the wavelength of 6.03 micrometers (or wave number of 1658 cm$^{-1}$) and its concentration in a sample.
Figure 3:
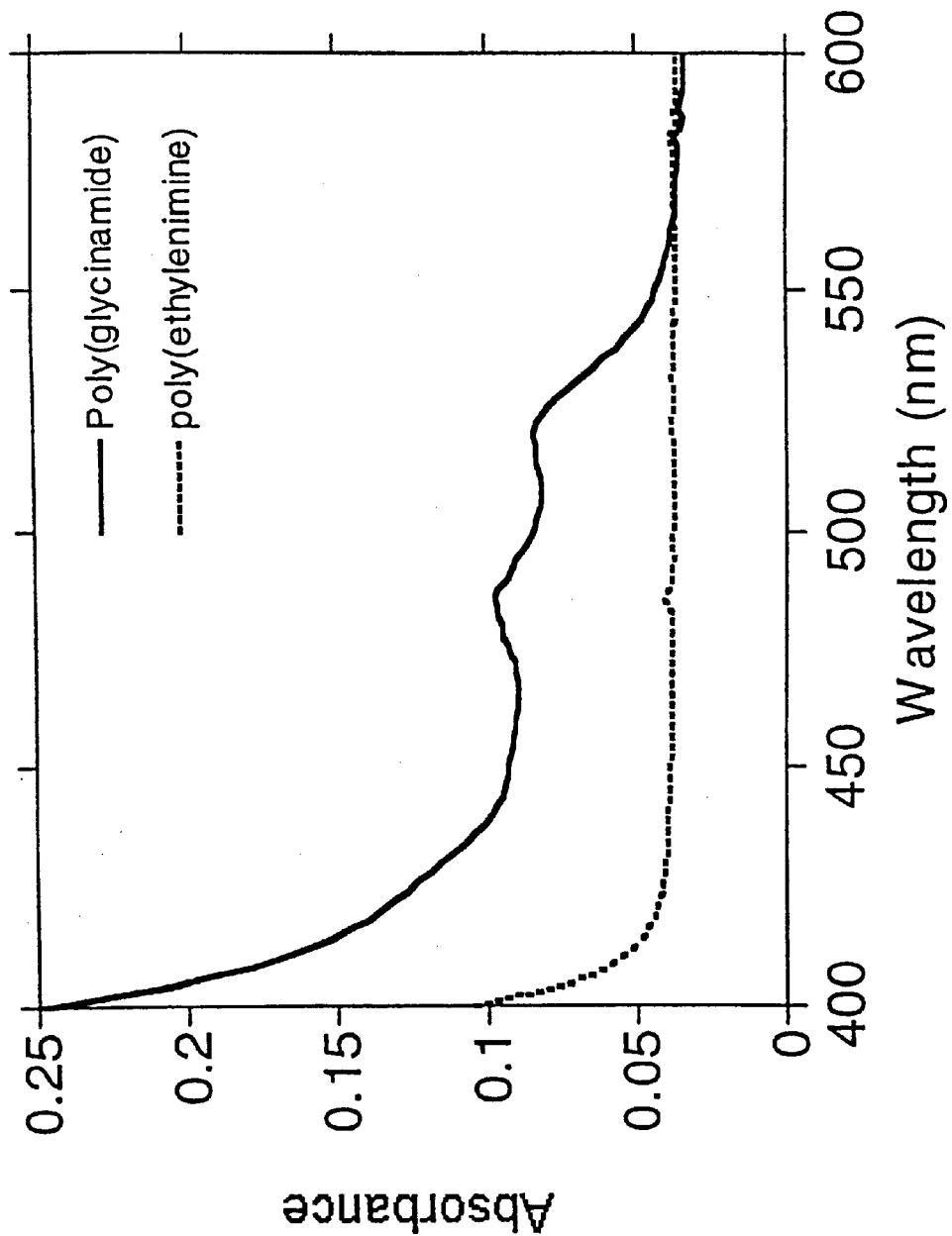
FIG. 3 shows the absorption spectra of the polyethylenimine reagent and the polyglycinamide reaction product of TCE.

Therefore, the reaction according to Equation 1 or 2 can provide the basis for detecting TCE by measuring the IR absorbance of the content of the capillary after the reaction at wavelength of 6.03 micrometers. FIG. 2 shows the correlation between the IR absorbance of a sample containing polyglycinamide at wavelength of 6.03 micrometers and the concentration of polyglycinamide in the same sample, which can be stoichiometrically related to the concentration of TCE that reacted.

Determination of Halogenated Hydrocarbons Using an Alternate Reagent

Halogenated hydrocarbons, such as TCE, trichloroethane ("TCA"), and trihalomethanes, are known to react with pyridine or alkyl-substituted compounds of pyridine to yield colored products in the presence of a strong base according the Fujiwara reaction (U.S. Pat. No. 5,547,877; the content of which is incorporated herein by reference). Colored reaction products of chloroform, bromodichloromethane, chlorodibromomethane, bromoform, and TCE strongly absorb at wavelength of 538–540 nm. Thus, an apparatus of the present invention can be used in conjunction with the Fujiwara reaction to provide a novel method for the determination of these and other halogenated hydrocarbons.

Determination of Pyridine and its Alkyl-Substituted Compounds

Conversely, a novel method for determination of pyridine or its alkyl-substituted compounds is provided by an apparatus of the present invention on the basis of the Fujiwara reaction using a halogenated hydrocarbon as the reagent, such as TCE, chloroform, bromoform, chlorodibromomethane, or bromodichloromethane, in the presence of a strong base such as sodium hydroxide, potassium hydroxide, or tetrabutylammonium hydroxide ("TBAH").

Determination of Polynitroaromatic Compounds

Polynitroaromatic compounds are known to react with ethylenediamine to yield products that exhibit strong absorbance in the visible wavelengths (D. J. Glover and E. G. Kayser, "Quantitative Spectrophotometric Analysis of Polynitroaromatic Compounds by Reaction With Ethylenediamine," Anal. Chem., Vol. 40, No. 13, 2055 (1968)). This reaction can be used in an apparatus or method of the present invention to determine the spatial or quantitative distribution of these compounds in an area of interest. For example, Table 1 shows the wavelengths at the absorbance maxima of selected polynitroaromatic compounds, which may be used as the basis for their identification in conjunction with an apparatus or method of the present invention.

TABLE 1

| Compound | Absorbance Maxima (nm) |
| --- | --- |
| 1,3,5-trinitrobenzene | 455, 540 |
| 2,4,6-trinitrobiphenyl | 455, 545 |
| 2,3',4,5',6-pentanitrobiphenyl | 450, 555 |
| 2,2',4,4',6,6'-hexanitrobiphenyl | 465, 530 |
| 2,4,6-trinitrotoluene | 465, 540 |
| 2,2',4,4',6,6'-hexatrinitrobiphenyl | 460, 550 |
| 2,2',4,4',6,6'-hexanitrostilbene | 460, 510 |
| 2,2',4,4'-tetranitrobiphenyl | 355, 545 |
| 3,3',5,5'-tetranitrobiphenyl | 450, 550 |
| 2,2',6,6'-tetranitrobiphenyl | 350, 560 |
| 1,4,5,8-tetranitronaphthalene | 320, 620 |

Determination of Polynitrobenzene and Substituted Compounds Thereof

The apparatus and method of the present invention may be used to determine the spatial and quantitative distribution of polynitrobenzene and selected substituted compounds thereof using the specified reagent for each chemical species to be detected to obtain a product having absorbance maxima shown in Table 2. (See, E. Sawicki, "Photometric Organic Analysis, Part 1," pp. 577–81, John Wiley and Sons, Inc., NY (1970).)

TABLE 2

| Compound | Reagent | Absorbance Maximum or Maxima (nm) |
| --- | --- | --- |
| 1,3-dinitrobenzene | Methanolic KOH and acetone | 559 |
| 1,3,5-trinitrobenzene | dibenzylketone or 2,5-pentadione | 500 |
| 2-ethoxy-1,3,5-trinitrobenzene | sodium hydroxide and methanol | 420, 478, 494 |
| 2-methyl-1,3-dinitrobenzene | Strong base and acetone | 555 |
| 2,4-dimethyl-1,3-dinitrobenzene | Strong base and acetone | 651 |

Determination of Selected Substituted Benzene

The apparatus and method of the present invention may be used to determine the spatial and quantitative distribution of selected substituted benzene compounds using the piperonal chloride as the reagent in the presence of a strong acid to obtain a product having absorbance maxima shown in Table 3 according to the following reaction. (See, E. Sawicki, "Photometric Organic Analysis, Part 1," p. 483, John Wiley and Sons, Inc., NY (1970).)

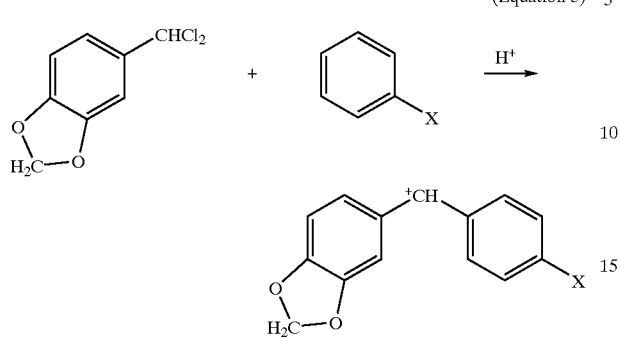

(Equation 3)

TABLE 3

| X | Absorbance Maximum (nm) |
|---|---|
| CH$_3$ | 513 |
| OCH$_3$ | 527 |
| C$_6$H$_5$ | 560 |
| SCH$_3$ | 575 |
| SC$_6$H$_5$ | 585 |

Determination of Selected Aromatic Aldehydes

The apparatus and method of the present invention may be used to determine the spatial and quantitative distribution of selected aromatic aldehydes using 2-nitrophenylhydrazine as the reagent in a mixture of 98% (by volume) of dimethylformamide and 2% (by volume) of a 10% (by volume) aqueous solution of tetraethylammonium hydroxide to obtain a product having absorbance maximum shown in Table 4. (See, E. Sawicki, "Photometric Organic Analysis, Part 1," pp. 568–73, John Wiley and Sons, Inc., NY (1970).)
Table 4

TABLE 4

| Compound | Absorbance Maximum (nm) |
|---|---|
| Benzaldehyde | 575 |
| 1-napthaldehyde | 600 |
| 9-anthraldehyde | 630 |
| 4-dimethylaminocinnamaldehyde | 435 |
| 2-nitrobenzaldehyde | 650 |
| 4-nitrobenzaldehyde | 665 |

Although the exemplary chemical species disclosed above are organic compounds, appropriate reagents may be used in an apparatus or a method of the present invention to identify and/or quantify inorganic compounds or inorganic/organic complexes.

While various embodiments are described herein, it will be appreciated from the specification that various combinations of elements, variations, equivalents, or improvements therein may be made by those skilled in the art, and are still within the scope of the invention as defined in the appended claims.

What is claimed is:

1. An apparatus for performing at least one of detecting a presence, determining a spatial distribution, and quantifying an amount of at least a chemical species, said apparatus comprising:

(1) a capillary having a wall that is permeable to said at least a chemical species, said capillary being substantially filled with a fluid medium comprising a reagent that is capable of undergoing a selective interaction with said at least a chemical species permeating through said wall to produce a product having a detectable characteristic of said interaction;

(2) a detector for detecting said characteristic of said interaction; and (3) a means for transferring a content of said capillary to said detector, said content comprising said fluid medium, and said means for transferring being capable of transferring said content in a substantial plug flow such that a time at which said characteristic of said interaction is detected provides a location of said interaction within said capillary, which location determines a location of said at least a chemical species outside said capillary.

2. The apparatus according to claim 1, wherein said detector is selected from the group consisting of detectors employing at least one method of detection selected from the group consisting of optical, spectroscopic, electrochemical, gravimetric, and mass spectrometric method.

3. The apparatus according to claim 2, wherein said optical method is selected from the group consisting of refractive index measurement and light scattering.

4. The apparatus according to claim 2, wherein said spectroscopic method is selected from the group consisting of measurements of UV-VIS electronic absorbance, Raman spectra, luminescence spectra, infrared spectra, and near-infrared spectra.

5. An apparatus for performing at least one of detecting a presence, determining a spatial distribution, and quantifying an amount of at least a chemical species, said apparatus comprising:

(1) a capillary having a wall that is permeable to said at least a chemical species, said capillary being substantially filled with a fluid medium comprising a reagent that is capable of undergoing a selective interaction with said at least a chemical species permeating through said wall to produce at least an optically detectable product; and (2) a detector for detecting said at least an optically detectable product; and (3) a means for transferring a content of said capillary to said detector for detecting said at least an optically detectable product, thereby detecting said at least a chemical species, said content comprising said at least an optically detectable interaction product, and said means for transferring being capable of transferring said content in a substantial plug flow such that a time at which said characteristic of said interaction is detected provides a location of said interaction within said capillary, which location determines a location of said at least a chemical species outside said capillary.

6. The apparatus according to claim 5, wherein said detector is capable of quantitatively relating an optical signal resulting from a presence of said at least an optically detectable product to said amount of said chemical species outside said capillary.

7. The apparatus according to claim 6, wherein said optical signal is selected from the group consisting of absorbance and intensity of emission of electromagnetic ("EM") radiation having a wavelength in a range from about 100 nm to about 1 mm.

8. The apparatus according to claim 5, wherein said capillary comprises a polymeric material selected from the group consisting of expanded polytetrafluoroethylene ("PTFE"), poly(vinyl chloride) ("PVC"), poly(vinyl alcohol) ("PVA"), polyurethane, polyolefins, polycarbonate, polystyrene, polyamide, poly(vinylidene fluoride) ("PVDF"), polyarylsuphones, polyacrylonitrile, polyether, poly(ether thioether), poly(methyl methacrylate), polyvinylpyrrolidone, polysiloxane, copolymer of perfluorosulfonic acid and polytetrafluoroethylene random copolymer of tetrafluoroethylene and perfluoro-2,2-dimethyl-1,3-dioxole, copolymers thereof, and blends thereof.

9. The apparatus according to claim 8, wherein said capillary is porous and has pore size in a range from about 1 nm to about 200 nm.

10. The apparatus according to claim 9, wherein said capillary preferably has pore size in a range from about 1 nm to about 50 nm.

11. The apparatus according to claim 8, wherein said capillary has an inner diameter in a range from about 2 micrometers to about 2 mm.

12. The apparatus according to claim 11, wherein said inner diameter is preferably in a range from about 0.1 mm to about 1.5 mm.

13. The apparatus according to claim 8, wherein said capillary has a wall thickness in a range from about 10 micrometers to about 200 micrometers.

14. The apparatus according to claim 13, wherein said wall thickness is preferably in a range from about 10 micrometers to about 150 micrometers.

15. The apparatus according to claim 5, wherein said capillary comprises a polymeric material deposited on a porous solid substrate; said polymeric material being selected from the group consisting of expanded polytetrafluoroethylene ("PTFE"), poly(vinyl chloride) ("PVC"), poly(vinyl alcohol) ("PVA"), polyurethane, polyolefins, polycarbonate, polystyrene, polyamide, poly(vinyidene fluoride) ("PVDF"), polyarylsuphones, polyacrylonitrile, polyether, poly(ether thioether), poly(methyl methacrylate), polyvinylpyrrolidone), polysiloxane, copolymer of perfluorosulfonic acid and polytetrafluoroethylene, random copolymer of tetrafluoroethylene and perfluoro-2,2-dimethyl-1,3-dioxole, copolymers thereof, and blends thereof.

16. The apparatus according to claim 15, wherein said porous solid substrate is a porous glass capillary.

17. The apparatus according to claim 5, wherein said chemical species is selected from the group consisting of halogenated hydrocarbons, polynitroaromatic hydrocarbons, mono-substituted benzene, aromatic aldehydes, aromatic amines, and mixtures thereof.

18. The apparatus according to claim 17, wherein said halogenated hydrocarbons are trichloroethylene, trichloroethane, chloroform, bromoform, chlorodibromomethane, and bromodichloromethane.

19. The apparatus according to claim 17, wherein said polynitroaromatic hydrocarbons are 1,3,5-trinitrobenzene; 2,4,6-trinitrobiphenyl; 2,3',4,5',6-pentanitrobiphenyl; 2,2'4, 4'6,6'-hexanitrobiphenyl; 2,4,6-trinitrotoluene; 2,2',4,4',6,6'-hexatrinitrobiphenyl 2,2',4,4',6,6'-hexanitrostilbene; 2,2',4, 4'-tetranitrobiphenyl; 3,3∝,5,5'-tetranitrobiphenyl; 2,2',6,6'-tetranitrobiphenyl; 1,4,5,8-tetranitronaphthalene; 1,3-dinitrobenzene; 2-ethoxy-1,3,5-trinitrobenzene; 2-methyl-1, 3-dinitrobenzene; 2,4-dimethyl-1,3-dinitrobenzene; and mixtures thereof.

20. The apparatus according to claim 17, wherein said mono-substituted benzene has a formula of Ar—X, wherein Ar is a phenyl radical and X is a radical selected from the group consisting of —$ch_3$, —$OCH_3$, —$C_6H_5$, —$SCH_3$, and —$SC_6H_6$.

21. The apparatus according to claim 17, wherein said aromatic aldehydes are benzaldehyde, 1-naphthaldehyde, 9-anthraldehyde, 4-dimethylaminocinnamaldehyde, 2-nitrobenzaldehyde, and 4-nitrobenzaldehyde.

22. The apparatus according to claim 17, wherein said aromatic amines are pyridine and alkyl-substituted pyridines.

23. The apparatus according to claim 5, wherein said chemical species is selected from the group consisting of halogenated hydrocarbons, polynitroaromatic hydrocarbons, mono-substituted benzene, aromatic aldehydes, aromatic amines, and mixtures thereof.

24. An apparatus for performing one of detecting a presence, determining a spatial distribution, and quantifying an amount of at least a chemical species, said apparatus comprising:

(1) a capillary having a wall that is permeable to said at least a chemical species, said capillary being substantially filled with a fluid medium comprising a reagent that is capable of undergoing a selective interaction with said at least a chemical species permeating through said wail to produce an optically detectable product;

(2) a detector for detecting said at least an optically detectable interaction product; and (3) a means for transferring a content of said capillary to said detector for detecting said at least an optically detectable interaction product, thereby detecting said at least a chemical species, said content comprising said at least an optically detectable product, and said means for transferring being capable of transferring said content in a substantial plug flow such that a time at which said characteristic of said interaction is detected provides a location of said interaction within said capillary, which location determines a location of said at least a chemical species outside said capillary;

wherein said capillary comprises a polymeric material selected from the group consisting of expanded polytetrafluoroethylene ("FTFE"), poly(vinyl chloride) ("PVC"), poly(vinyl alcohol) ("PVA"), polyurethane, polyolefins, polycarbonate, polystyrene, polyamide, poly(vinylidene fluoride) ("PVDF"), polyarylsuphones, polyacrylonitrile, polyether, poly(ether thioether), poly(methyl methacrylate), polyvinylpyrrolidone, polysiloxane, copolymer of perfluorosulfonic acid and polytetrafluoroethylene, random copolymer of tetrafluoroethylene and perfluoro-2,2-dimethyl-1,3-dioxole, copolymers thereof, and blends thereof; said detector is capable of quantitatively relating an optical signal resulting from a presence and an amount of said at least one optically detectable reaction product to said presence and said amount of said chemical species outside said capillary; and said optical signal is selected from the group consisting of absorbance and emission of EM radiation having a wavelength in a range from about 100 nm to about 1 mm.

* * * * *